US012735737B2

(12) United States Patent
Walker et al.

(10) Patent No.: US 12,735,737 B2
(45) **Date of Patent: *Sep. 15, 2026**

(54) FAR-RED DYE PROBE FORMULATIONS

(71) Applicant: Gen-Probe Incorporated, San Diego, CA (US)

(72) Inventors: Sheila Aubin Walker, San Diego, CA (US); Mehrdad R. Majlessi, Escondido, CA (US); Jimmykim Pham, San Diego, CA (US); Joshua Bousquet, Vista, CA (US)

(73) Assignee: Gen-Probe Incorporated, San Diego, CA (US)

( * ) Notice: Subject to any disclaimer, the term of this patent is extended or adjusted under 35 U.S.C. 154(b) by 788 days.

This patent is subject to a terminal disclaimer.

(21) Appl. No.: 18/046,261

(22) Filed: Oct. 13, 2022

(65) Prior Publication Data

US 2023/0203581 A1 Jun. 29, 2023

Related U.S. Application Data

(63) Continuation of application No. 16/269,307, filed on Feb. 6, 2019, now Pat. No. 11,499,193.

(60) Provisional application No. 62/627,040, filed on Feb. 6, 2018.

(51) Int. Cl.

*C12Q 1/6876* (2018.01)
*C09B 23/08* (2006.01)
*C12Q 1/6818* (2018.01)

(52) U.S. Cl.

CPC .......... *C12Q 1/6818* (2013.01); *C09B 23/083* (2013.01); *C12Q 1/6876* (2013.01)

(58) Field of Classification Search

CPC .................................................... C12Q 1/6876
See application file for complete search history.

(56) References Cited

U.S. PATENT DOCUMENTS

| | | | | |
|---|---|---|---|---|
| 9,139,870 | B2 | 9/2015 | Nelson et al. | |
| 11,499,193 | B2 * | 11/2022 | Aubin-Walker | C12Q 1/6876 |
| 2003/0044353 | A1 | 3/2003 | Weissleder et al. | |
| 2006/0068399 | A1 | 3/2006 | McMillan et al. | |
| 2008/0026382 | A1 | 1/2008 | Wang | |
| 2008/0064071 | A1 | 3/2008 | Hogrefe et al. | |
| 2010/0209973 | A1 | 8/2010 | Kim et al. | |
| 2011/0159497 | A1 | 6/2011 | Lee et al. | |
| 2013/0274437 | A1 | 10/2013 | Duan et al. | |
| 2013/0280695 | A1 | 10/2013 | Hillebrand et al. | |
| 2015/0184145 | A1 | 7/2015 | Angrish et al. | |
| 2016/0096869 | A1 * | 4/2016 | Hansen | A61K 47/6415 424/9.1 |
| 2017/0183720 | A1 * | 6/2017 | Gupta | C12Q 1/6853 |
| 2019/0241956 | A1 | 8/2019 | Aubin-Walker et al. | |

FOREIGN PATENT DOCUMENTS

| | | | | |
|---|---|---|---|---|
| CN | 103540660 | A | 1/2014 | |
| CN | 103805706 | * | 2/2014 | C12Q 1/686 |
| CN | 103805706 | A | 5/2014 | |
| JP | 2013503951 | A | 2/2013 | |
| WO | 2003062824 | A1 | 7/2003 | |
| WO | 2007005626 | A1 | 1/2007 | |
| WO | 2011097248 | A1 | 8/2011 | |
| WO | 2016129951 | A1 | 8/2016 | |

OTHER PUBLICATIONS

Trademark registration for TAQMAN(R), (Year: 2017).*
Wang et al., "Stabilizing two IgG1 monoclonal antibodies by surfactants: Balance between aggregation prevention and structure perturbation" European Journal of Pharmaceutics and Biopharmaceutics vol. 114 pp. 263-277, DOI:10.1016/j.ejpb.2017.01.025 (Year: 2017).*
English machine translation of CN103805706, downloaded from worldwide.espacenet.com (Year: 2014).*
Täpp et al., "Homogeneous Scoring of Single-Nucleotide Polymorphisms: Comparison of the 5'-Nuclease TaqMan® Assay and Molecular Beacon Probes" Bio Techniques vol. 28:4, pp. 732-738, DOI:10.2144/00284rr02 (Year: 2000).*
Office Action in corresponding Japanese Application No. 2020564049 dated Dec. 20, 2022 (13 pages).
USPTO Non-Final Office Action in U.S. Appl. No. 16/269,307 dated May 5, 2021 (15 pages).
USPTO Non-Final Office Action in U.S. Appl. No. 16/269,307 dated Sep. 15, 2021 (11 pages).
Office Action in corresponding European Application No. 19706191.4 dated Jun. 7, 2022 (6 pages).
A Guide to Fluorochromes, Abcam, p. 1 (2012).
Alexander et al., "Low-Surface Energy Surfactants with Branched Hydrocarbon Architectures," Langmuir, 30: 3413-3421 (2014).
Alexander et al., "Low-Surface Energy Surfactants with Branched Hydrocarbon Architectures," Langmuir, 30: 3413-3421, supplemental material p. 1-12 (2014).
Applied Biosystems Publication No. 4474507, DNA Fragment Analysis by Capillary Electrophoresis, p. 1-220 (2014).
ATTO-TEC catalog "Fluorescent Labels and Dyes," p. 1-47 (2009).
Biocompare CY5 Dyes (pp. 1-6); downloaded from https://www.biocompare.com/26061-Cy5-Dyes/ (2021).
Click Chemistry Tools, Cy5 NHS Ester, pp. 1-3, downloaded from https://clickchemistrytools.com/product/cy5-nhs-ester/ on Sep. 9, 2021 ( Year: 2021).
Microsynth "trademarks and Disclaimers", p. 1, downloaded from https://www.microsynth.com/trademarks-disclaimers. html on Sep. 9, 2021 (Year: 2021).
PCT, International Preliminary Report on Patentability dated Aug. 11, 2020 from corresponding PCT International Application PCT/US2019/016890 (7 pages).
PCT, International Search Report and Written Opinion dated Apr. 29, 2019 from corresponding PCT International Application PCT/US2019/016890 (12 pages).

(Continued)

*Primary Examiner* — Andrea Olson

(74) *Attorney, Agent, or Firm* — Sherbina Intellectual Property Law, PLLC; Nicholas V. Sherbina; Jeffrey E. Landes

(57) ABSTRACT

Disclosed are formulations, including both liquid and lyophilized formulations, comprising a far-red dye probe and a non-linear surfactant or foamban. Also disclosed are related methods for preparing a lyophilized far-red dye probe formulation as well as related kits and diagnostic products.

12 Claims, No Drawings

Specification includes a Sequence Listing.

(56) References Cited

OTHER PUBLICATIONS

SETA Fluorsecence Lifetime Dyes, p. 1-2, downloaded from www.setabiomedicals.com/files/Pdf/SETA_Lifetime%20Dyes.pdf on Apr. 28, 2021.
Sigma-Aldrich, "Zwitterionic Detergents," p. 1-3 from www.sigmaaldrich.com/life-science/biochemicals/biochemicals-products.html?TablePage=14572925 in Apr. 28, 2021.
Umezawa et al., "Bright, Color-Tunable Fluorescent Dyes in the Vis/NIR Region: Establishment of New "Tailor-Made" Multicolor Fluorophores Based on Borondipyrromethene," Chemistry: A European Journal, 15: 1096-1106 (2009).
Extended European Search Report dated Dec. 20, 2024, issued in corresponding European Application No. 24202599.7, filed Feb. 6, 2019 (11 pages).
Examination Report dated Sep. 23, 2025, issued in corresponding European Application No. 24202599.7, filed Feb. 6, 2019 (9 pages).
Examination Report dated Oct. 9, 2025, issued in corresponding Australian Application No. 2025226763, filed Sep. 4, 2025 (3 pages).
Office Action dated Jun. 28, 2024, issued in corresponding Chinese Application No. 2019800117336, filed Feb. 6, 2019.

* cited by examiner

FAR-RED DYE PROBE FORMULATIONS

CROSS-REFERENCE TO RELATED APPLICATIONS

This application is a continuation application Ser. No. 16/269,307, filed Feb. 6, 2019, which claims benefit of priority under 35 U.S.C § 119(e) to provisional application No. 62/627,040, filed Feb. 6, 2018, the contents of which is hereby incorporated by reference herein in its entirety.

REFERENCE TO SEQUENCE LISTING

The instant application contains a Sequence Listing which has been submitted in ASCII format via EFS-Web and is hereby incorporated by reference in its entirety. Said ASCII Copy, created on Aug. 9, 2022, is named "2022-08-09_01159-0042-01US_Seq_List_ST26" and is 34,640 bytes in size.

BACKGROUND

Probes comprising far-red fluorescent dyes are widely used in many bioscience applications, including, for example, in vitro detection assays, traditional and super-resolution localization microscopy, and live cell imaging. Far-red fluorescent dyes are also particularly convenient for multiplexing due to their limited spectral overlap with other commonly used fluorophores and fluorescent proteins. Formulation of far-red dye probes, however, presents significant challenges due to a significant loss of fluorescent signal after reconstitution and/or storage in aqueous form.

SUMMARY

In one aspect, the present invention provides a stabilized far-red dye probe formulation. In some embodiments, the formulation generally includes a far-red dye probe comprising a far-red dye conjugated to a carrier molecule, a non-linear surfactant at a concentration of greater than about 0.05% (v/v), and at least one buffering agent, where the formulation is an aqueous solution. In other embodiments, the formulation generally includes a far-red dye probe comprising a far-red dye conjugated to a carrier molecule, foamban at a concentration of greater than about 0.05% (v/v), and at least one buffering agent, where the formulation is an aqueous solution. A suitable buffering agent is Tris; in some such variations, the Tris buffering agent is present at a concentration of from about 5 mM to about 50 mM. Particularly suitable far-red dyes include far-red cyanine dyes such as, e.g., cyanine 5 or cyanine 5.5.

In certain embodiments of a stabilized far-red dye probe formulation comprising a non-linear surfactant as above, the non-linear surfactant is a polyoxyethylene sorbitan fatty acid ester such as, for example, polysorbate 20, polysorbate 40, or polysorbate 60. In other variations, the non-linear surfactant is digitonin. Suitable non-linear surfactant concentrations include concentrations of from about 0.06% (v/v) to about 20% (v/v), from about 0.06% (v/v) to about 10% (v/v), from about 0.1% (v/v) to about 20% (v/v), or from about 0.1% (v/v) to about 10% (v/v). In some embodiments, the non-linear surfactant concentration is from about 0.5% (v/v) to about 20% (v/v), from about 0.5% (v/v) to about 10% (v/v), from about 1% (v/v) to about 20% (v/v), or from about 1% (v/v) to about 10% (v/v), or from about 1% (v/v) to about 2% (v/v).

In some embodiments of a stabilized far-red dye probe formulation as above, the carrier molecule is a nucleic acid such as, for example, an RNA. In other, non-mutually exclusive embodiments, the far-red dye probe further includes a quencher; in some such variations, the far-red dye probe is a molecular torch, a molecular beacon, or a TaqMan probe. In some nucleic acid probe embodiments, the formulation further includes a first amplification oligomer, where (i) the far-red dye probe comprises a target-hybridizing sequence that specifically binds to a first sequence contained within a target region of a target nucleic acid, (ii) the first amplification oligomer comprises a target-hybridizing sequence that specifically binds to a second sequence contained within the target region, and (iii) the first amplification oligomer is configured to produce, in an amplification assay comprising the target nucleic acid as a template, an amplification product containing the target region. In some embodiments further containing a first amplification oligomer as above, the formulation further includes a second amplification oligomer comprising a target-hybridizing sequence that specifically binds to a third sequence contained within the target region, where the first and second amplification oligomers are configured to amplify the target region in multiple cycles of the amplification assay. In some variations of a formulation further containing a first amplification oligomer, the first amplification oligomer is a promoter-based amplification oligomer further comprising a promoter sequence located 5' to the first target-hybridizing sequence. A formulation comprising a nucleic acid far-red dye probe and further containing a first amplification oligomer as above may further include one or more additional components suitable for performing the amplification assay such as, e.g., one or more nucleotide triphosphates and/or one or more salts or co-factors.

In another aspect, the present invention provides a method of preparing a stabilized, lyophilized far-red dye probe formulation. The method generally includes (a) providing a stabilized far-red dye probe formulation as above, and (b) lyophilizing the aqueous solution to form the lyophilized far-red dye probe formulation. In another aspect, the present invention provides a stabilized, lyophilized far-red dye probe formulation prepared by the foregoing method.

In another aspect, the present invention provides a stabilized, lyophilized far-red dye probe formulation that enables reconstitution into an aqueous formulation as set forth above.

In another aspect, the present invention provides a kit comprising (i) a first sealed container containing a lyophilized far-red dye probe formulation as above and (ii) a second sealed container containing a diluent. In some embodiments, the diluent comprises the non-linear surfactant or foamban; in some such embodiments, the non-linear surfactant or foamban is present in the diluent at a concentration of greater than about 0.05% (v/v) (e.g., from about 0.06% (v/v) to about 20% (v/v), from about 0.1% (v/v) to about 10% (v/v), or from about 0.5% (v/v) to about 5% (v/v)).

In still another aspect, the present invention provides a method of preparing a stabilized, aqueous far-red dye probe formulation. In some embodiments, the method generally includes (a) providing a lyophilized far-red dye probe formulation as above; and (b) dissolving the lyophilized far-red dye probe formulation in a diluent to provide a reconstituted formulation. In some embodiments, the diluent comprises the non-linear surfactant or foamban; in some such embodiments, the non-linear surfactant or foamban is present in the diluent at a concentration of greater than about 0.05% (v/v)

(e.g., from about 0.06% (v/v) to about 20% (v/v), from about 0.1% (v/v) to about 10% (v/v), or from about 0.5% (v/v) to about 5% (v/v)).

In other embodiments, a method of preparing a stabilized, aqueous far-red dye probe formulation generally includes (a) providing a lyophilized far-red dye probe formulation that enables reconstitution into an aqueous solution comprising at least one buffering agent and a far-red dye probe comprising a far-red dye conjugated to a carrier molecule, and (b) dissolving the lyophilized far-red dye probe formulation in a diluent to provide a reconstituted formulation, where at least one of the lyophilized far-red dye probe formulation and the diluent comprises a non-linear surfactant or foamban, and where the reconstituted formulation comprises the non-linear surfactant or foamban at a concentration of greater than about 0.05% (v/v). In some embodiments, both the lyophilized far-red dye probe formulation and the diluent comprise the non-linear surfactant or foamban. In some embodiments, the method further includes preparing the lyophilized far-red dye probe formulation by lyophilizing an aqueous solution comprising the far-red dye probe and the at least one buffering agent.

In another aspect, the present invention provides a kit comprising (i) a first sealed container containing a lyophilized far-red dye probe formulation that enables reconstitution into an aqueous solution comprising at least one buffering agent and a far-red dye probe comprising a far-red dye conjugated to a carrier molecule, and (ii) a second sealed container containing a diluent, where at least one of the lyophilized far-red dye probe formulation and the diluent comprises a non-linear surfactant or foamban, and where reconstitution of the lyophilized far-red dye probe formulation in the diluent provides a final non-linear surfactant or foamban concentration of greater than about 0.05% (v/v). In some embodiments, both the lyophilized far-red dye probe formulation and the diluent comprise the non-linear surfactant or foamban.

In still another aspect, the present invention provides a diagnostic product comprising a sealed container containing a stabilized far-red dye probe formulation as set forth above. These and other aspects of the invention will become evident upon reference to the following detailed description of the invention.

Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise.

The term "far-red dye," as used herein, refers to a fluorescent molecule that has an emission maximum from about 630 nm to about 800 nm. In some embodiments, a far-red dye has an emission maximum from about 630 nm to about 750 nm, from about 640 nm to about 750 nm, from about 630 nm to about 700 nm, from about 640 nm to about 700 nm, from about 630 nm to about 680 nm, or from about 640 nm to about 680 nm. Typically, far-red dyes are excited by long wavelength excitation sources (e.g., laser sources providing a wavelength of about 625 nm to about 655 nm).

The term "carrier molecule," as used herein, refers to a biological or a non-biological component that can be covalently bonded to a far-red dye. Labeled carrier molecules are useful as probes for monitoring or detecting one or more in vitro, in situ, or in vivo biological or biochemical targets, processes, or reactions. Such components may include, for example, a nucleoside, a nucleotide, an oligonucleotide, a nucleic acid, an amino acid, a peptide, a protein, a polysaccharide, a drug, a hormone, a lipid, a lipoprotein, a lipid assembly, a synthetic polymer, a polymeric microparticle, and combinations thereof. In some variations, a carrier molecule comprises a moiety or region that is capable of a specific binding interaction with another molecule (e.g., a target-hybridizing sequence of a nucleic acid carrier molecule, or a binding site of a protein such as, for example, an antigen-binding site an antibody).

"Covalently bonded," as used herein, indicates a direct covalent linkage or through a number of atoms corresponding to a linker moiety.

The term "stabilized," in reference to a lyophilized far-red dye probe formulation containing a surfactant as described herein, means that the far-red dye probe formulation, when used in a detection assay at the time of reconstitution into aqueous form from the lyophilized form (day 0) and at 30 days following reconstitution and storage of the reconstituted formulation at 2-8° C. during the 30 days (day 30), exhibits less than about a 20% drop in relative fluorescence units (RFU) at day 30 relative to day 0. When used to refer to an aqueous far-red dye probe formulation containing a surfactant as described herein, the term "stabilized" means that the aqueous far-red dye probe formulation either (a) is reconstituted from a stabilized, lyophilized formulation as defined above or (b) can be lyophilized to yield a stabilized, lyophilized formulation as defined above. In some variations, a stabilized far-red dye probe formulation exhibits less than about a 15% RFU drop, less than about a 12% drop, or less than about a 10% RFU drop.

The term "non-linear surfactant," as used herein, means a surfactant having a branched chain structure. A non-linear surfactant may include one or more ring structures, which may be, for example, in a principal chain and/or in one or more branch chains. Exemplary non-linear surfactant include polysorbate 20, polysorbate 40, polysorbate 60, and digitonin. In certain variations, a non-linear surfactant is non-ionic.

The term "stabilizing surfactant," as used herein, means a non-linear surfactant or foamban.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see PCT No. WO 95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine, 5-methylisocytosine, isoguanine; The Biochemistry of the Nucleic Acids 5-36, Adams et al., ed., $11^{th}$ ed., 1992, Abraham et al., 2007, BioTechniques 43: 617-24), which include derivatives of purine or pyrimidine bases (e.g., $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo[3,4-d]pyrimidine; U.S. Pat. Nos. 5,378,825, 6,949,367 and PCT No. WO 93/13121). Nucleic acids may include "abasic" residues in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., Biochemistry 43:13233-41, 2004). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well-known in the art although nucleic acids may be purified from natural sources using routine techniques.

A "nucleotide," as used herein, is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me).

A "target nucleic acid," as used herein, is a nucleic acid comprising a target sequence to be detected. Target nucleic acids may be DNA or RNA as described herein, and may be either single-stranded or double-stranded. The target nucleic acid may include other sequences besides the target sequence.

The term "target sequence," as used herein, refers to the particular nucleotide sequence of a target nucleic acid that is to be detected. The "target sequence" includes the complexing sequences to which oligonucleotides (e.g., probe oligonucleotide, priming oligonucleotides and/or promoter oligonucleotides) complex during a detection process (e.g., an amplification-based detection assay such as, for example, TMA or PCR). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality of strains within a species (e.g., various strains of a bacterial or viral species). It is understood that other reasons exist for configuring a target-hybridizing sequence to have less than 100% complementarity to a target nucleic acid.

The term "region," as used herein, refers to a portion of a nucleic acid wherein said portion is smaller than the entire nucleic acid. For example, when the nucleic acid in reference is a promoter-based amplification oligomer, the term "region" may be used refer to the smaller promoter portion of the entire oligonucleotide. Similarly, and also as example only, when the nucleic acid is a target nucleic acid, the term "region" may be used to refer to a smaller area of the nucleic acid, wherein the smaller area is targeted by one or more oligonucleotides.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., a far-red dye).

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter primer" or "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence.

"Promoter-based amplification oligomer," as used herein, means either a promoter primer or promoter provider.

As used herein, a "promoter" is a specific nucleic acid sequence that is recognized by a DNA-dependent RNA polymerase ("transcriptase") as a signal to bind to the nucleic acid and begin the transcription of RNA at a specific site.

"Amplification" refers to any known procedure for obtaining multiple copies of a target nucleic acid sequence or its complement or fragments thereof. The multiple copies may be referred to as amplicons or amplification products. Known amplification methods include both thermal cycling and isothermal amplification methods. In some embodiments, isothermal amplification methods are preferred. Replicase-mediated amplification, polymerase chain reaction (PCR), ligase chain reaction (LCR), strand-displacement amplification (SDA), and transcription-mediated or transcription-associated amplification are non-limiting examples of nucleic acid amplification methods. Replicase-mediated amplification uses self-replicating RNA molecules, and a replicase such as QB-replicase (e.g., U.S. Pat. No. 4,786,600). PCR amplification uses a DNA polymerase, pairs of primers, and thermal cycling to synthesize multiple copies of two complementary strands of dsDNA or from a cDNA (e.g., U.S. Pat. Nos. 4,683,195, 4,683,202, and 4,800,159). LCR amplification uses four or more different oligonucleotides to amplify a target and its complementary strand by using multiple cycles of hybridization, ligation, and denaturation (e.g., U.S. Pat. Nos. 5,427,930 and 5,516,663). SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. Nos. 5,422,252; 5,547,861; and 5,648,211). Amplification methods include embodiments suitable for the amplification of RNA target nucleic acids, such as transcription-mediated amplification (TMA) or NASBA "Transcription-associated amplification," also referred to herein as "transcription-mediated amplification" (TMA), refers to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. Variations of transcription-associated amplification are well-known in the art as previously disclosed in detail (e.g., U.S. Pat. Nos. 4,868,105; 5,124,246; 5,130,238; 5,399,491; 5,437,990; 5,554,516; and 7,374,885; and PCT Pub. Nos. WO 88/01302, WO 88/10315, and WO 95/03430).

The term "amplicon," which is used interchangeably with "amplification product," refers to the nucleic acid molecule generated during an amplification procedure that is complementary or homologous to a sequence contained within the target sequence. These terms can be used to refer to a single strand amplification product, a double strand amplification product or one of the strands of a double strand amplification product.

"Detection oligonucleotide" and "detection probe oligomer" are used interchangeably herein to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Detection probe oligomers may be DNA, RNA, analogs thereof or combinations thereof. A detection probe oligomer's "target sequence" generally refers to a smaller nucleic acid sequence within a larger nucleic acid sequence that hybridizes specifically to at least a portion of a probe oligomer by standard base pairing. A detection probe oligomer may comprise target-specific sequences and other sequences that contribute to the three-dimensional conformation of the probe (e.g., U.S. Pat. Nos. 5,118,801; 5,312,728; 6,849,412; 6,835,542; 6,534,274; and 6,361,945; and US Pub. No. 20060068417).

The term "TaqMan probe" refers to detection oligonucleotides that contain a fluorescent dye, typically on the 5' base, and a non-fluorescent quenching dye (quencher), typically on the 3' base. When irradiated, the excited fluorescent dye transfers energy to the nearby quenching dye molecule rather than fluorescing, resulting in a non-fluorescent substrate. During amplification, the exonuclease activity of the polymerase cleaves the TaqMan probe to separate the fluorophore from the quencher, thereby allowing an unquenched signal to be emitted from the fluorophore as an indicator of amplification.

As used herein, structures referred to as "molecular torches" are designed to include distinct regions of self-complementarity ("the closing domain") which are connected by a joining region ("the target binding domain") and which hybridize to one another under predetermined hybridization assay conditions. All or part of the nucleotide sequences comprising target closing domains may also function as target binding domains. Thus, target closing sequences can include, target binding sequences, non-target binding sequences, and combinations thereof.

A "polypeptide" or "polypeptide chain" is a polymer of amino acid residues joined by peptide bonds, whether produced naturally or synthetically. Polypeptides of about 25 amino acid residues or less are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell.

A "peptide aptamer" is a peptide that specifically binds to a target protein and which is embedded as a loop within a protein scaffold. See generally, e.g., Li et al., Curr. Med. Chem. 18:4215-4222, 2011.

As used herein, the term "antibody" refers to any immunoglobulin protein that specifically binds to an antigen, as well as antigen-binding fragments thereof and engineered variants thereof. Hence, the term "antibody" includes, for example, polyclonal antibodies, monoclonal antibodies, and antigen-binding antibody fragments that contain the paratope of an intact antibody, such as Fab, Fab', F(ab')2 and F(v) fragments. Genetically engineered intact antibodies and fragments, such as chimeric antibodies, humanized antibodies, single-chain FIT fragments, single-chain antibodies, diabodies, minibodies, linear antibodies, multivalent or multispecific hybrid antibodies, and the like are also included. Thus, the term "antibody" is used expansively to include any protein that comprises an antigen binding site of an antibody and is capable of binding to its antigen.

The term "diluent" as used herein refers to a solution suitable for altering or achieving an exemplary or appropriate concentration or concentrations as described herein.

The term "container" refers to something into which an object or liquid can be placed or contained, e.g., for storage (for example, a holder, receptacle, vessel, or the like).

Reference to a numerical range herein (e.g., "X to Y" or "from X to Y") includes the endpoints defining the range and all values falling within the range.

Unless otherwise apparent from the context, when a value is expressed as "about" X or "approximately" X, the stated value of X will be understood to be accurate to ±10%.

DESCRIPTION

The present invention provides stabilized formulations of far-red dye probes comprising a surfactant selected from a non-linear surfactant and foamban. The formulations are based, in part, on the surprising observation that the surfactant-containing formulations exhibit a decrease in loss of the far-red dye probe's fluorescence signal intensity (RFUs) when stored over time in aqueous form, as compared to formulations not containing the stabilizing surfactant. Without intending to be bound by theory, the present inventors believe that a far-red dye probe in buffer in the absence of a stabilizing surfactant tends to aggregate over time to form an organized structure (e.g., a micelle) in which the more non-polar fluorophore molecules come in very close contact and self-quench, and that in the presence of the stabilizing surfactant (e.g., a non-polar, non-linear surfactant), aggregation of the far-red dye probe is disrupted so that the fluorophore molecules are no longer in close proximity and thus can no longer self-quench. Particularly suitable non-linear surfactants include polyoxyethylene sorbitan fatty acid esters (e.g., polysorbate 20, polysorbate 40, and polysorbate 60) and digitonin.

In certain embodiments, the stabilized far-red dye probe formulation is an aqueous formulation. Such formulations may be, for example, a pre-lyophilized formulation or one that has been reconstituted from a lyophilized form. In some variations, the formulation is provided as an aqueous solution containing a far-red dye probe comprising a far-red dye conjugated to a carrier molecule, a surfactant at a concentration of greater than about 0.05% (v/v), where the surfactant is selected from a non-linear surfactant and foamban, and at least one buffering agent. In some embodiments, the surfactant is present at a concentration of from about 0.06% (v/v) to about 20% (v/v), from about 0.06% (v/v) to about 10% (v/v), from about 0.06% (v/v) to about 3% (v/v), from about 0.1% (v/v) to about 20% (v/v), from about 0.1% (v/v) to about 10% (v/v), from about 0.1% (v/v) to about 3% (v/v), from about 0.5% (v/v) to about 20% (v/v), from about 0.5% (v/v) to about 10% (v/v), from about 0.5% (v/v) to about 3% (v/v), from about 1% (v/v) to about 20% (v/v), from about 1% (v/v) to about 10% (v/v), or from about 1% (v/v) to about 3% (v/v). In more specific variations, the surfactant is present at a concentration of about 0.41% (v/v), about 0.62% (v/v), about 1% (v/v), about 1.24% (v/v), about 1.5% (v/v), about 1.6% (v/v), or about 3% (v/v).

A buffering agent is typically present at a concentration sufficient to maintain a pH suitable for use of the far-red dye probe in a biological system such as, e.g., an in vitro or in situ assay. In some embodiments, a buffering agent is present at a concentration sufficient to maintain a pH in the range of from about 5.5 to about 8.5, from about 6.0 to about 8.0, from about 6.5 to about 8.0, or from about 6.5 to about 7.5. Suitable buffering agents include Tris (2-amino-2-(hydroxymethyl)-1,3-propanediol), PIPES (piperazine-N,N'-bis (2-ethanesulfonic acid)), HEPES (4-(2-hydroxyethyl)-1-piperazineethanesulfonic acid), phosphate, citrate, succinate, and histidine. In certain embodiments, a Tris buffering agent is present at a concentration of about 5 mM to about 50 mM or about 10 mM to about 50 mM. Other suitable concentrations of buffers for formulations in accordance with the present invention can be readily determined by one of ordinary skill in the art.

In certain variations, formulations—such as those suitable for lyophilization, reconstituted from lyophilized form, or a lyophilized formulation for reconstitution into an aqueous formulation as described herein—may contain a lyoprotectant. Exemplary lyoprotectants include glycerol; non-reducing sugars such as, e.g., sucrose, raffinose, or trehalose; and amino acids such as, e.g., glycine, arginine, or methionine. The use of lyoprotectants, including selection of appropriate concentrations to prevent unacceptable amounts of degradation and/or aggregation of a carrier molecule upon lyophilization, is generally well-known in the art. In some variations where the lyoprotectant is glycerol, the lyoprotectant concentration in an aqueous formulation ranges from about 1% (v/v) to about 10% (v/v), from about 2% (v/v) to about 8% (v/v), or from about 2% (v/v) to about 5% (v/v).

Concentrations of far-red dye probe in stabilized formulations as described herein may vary depending on the particular probe carrier molecule and the desired use, and suitable probe concentrations may be readily determined by a skilled artisan in the context of a particular application. In certain variations, a far-red dye probe (e.g., a far-red dye probe comprising a nucleic acid carrier molecule) is present in a stabilized formulation at a concentration of from about 0.01 μM to about 50 mM, from about 0.01 μM to about 5 mM, from about 0.05 μM to about 500 μM, from about 0.05 μM to about 100 μM, from about 0.1 μM to about 100 μM, or from about 0.1 μM to about 50 μM. In other variations, a far-red dye probe (e.g., a far-red dye probe comprising a nucleic acid carrier molecule) is present in a stabilized formulation at a concentration of from about 0.001 mg/mL to about 100 mg/mL, from about 0.001 mg/mL to about 50 mg/mL, from about 0.01 mg/mL to about 25 mg/mL, or from about 0.01 mg/mL to about 10 mg/mL.

Suitable far-red dyes for use in accordance with the present invention include cyanine 5 (CY5®), cyanine 5.5 (CY5.5®), ALEXA FLUOR® 633, ALEXA FLUOR® 635, ALEXA FLUOR® 647, QUASAR® 705, QUASAR® 650, DYLIGHT® 649, DYLIGHT® 650, HILYTE™ 647, ATTO™ 647, and Allophycocyanin (APC). CyLyte Fluor dyes and HILYTE Fluor dyes are available from AnaSpec, Inc., Fremont, CA. ALEXA FLUOR dyes are available from Thermo Fisher Scientific, Waltham, MA. ATTO™ 647, and Allophycocyanin (APC) are available from Millipore-Sigma, St. Louis, MO. Cyanine 5 and Cyanine 5.5 are available from Glen Research, Sterling, VA. QUASAR 650 and QUASAR 705 are available from LGC Biosearch Technologies, Petaluma, CA. Additional vendors include, but are not limited to, Dyomics (Jena, Germany) and Atto- Tec GmbH (Siegen-Weidenau, Germany). In some embodiments, the far-red dye is a far-red cyanine dye such as, for example, CY5®, CY5.5®, ALEXA FLUOR 647, or ATTO 647.

A variety of carrier molecules may be used in accordance with the present invention. Suitable carrier molecules may include nucleosides, nucleotides, nucleic acids (e.g., oligonucleotides), amino acids, proteins (e.g., peptides, antibodies), polysaccharides, hormones, drugs, lipids, lipoproteins, lipid assemblies, synthetic polymers, polymeric microparticles, and combinations thereof. Particularly suitable are carrier molecules comprising a moiety or region that is capable of a specific binding interaction with another molecule.

In certain variations, the probe carrier molecule is a nucleic acid that specifically binds to a target molecule such as, e.g., a target nucleic acid. Particularly suitable nucleic acid carrier molecules include oligonucleotides comprising a target-hybridizing sequence that specifically binds to a target sequence contained with a target region of target nucleic acid. Oligonucleotide carrier molecules may be, e.g., DNA or RNA oligomers, or oligomers that contain a combination of DNA and RNA nucleotides, or oligomers synthesized with a modified backbone, e.g., an oligomer that includes one or more 2'-methoxy substituted ribonucleotides. In some embodiments, a probe comprising an oligonucleotide carrier molecule includes a quencher in addition to a far-red dye, a combination that is particularly useful in fluorescence resonance energy transfer (FRET) assays; specific variations of such probes include, e.g., a TaqMan detection probe (Roche Molecular Diagnostics) and a "molecular beacon" (see, e.g., Tyagi et al., Nature Biotechnol. 16:49-53, 1998; U.S. Pat. Nos. 5,118,801 and 5,312,728; each incorporated by reference herein).

An oligonucleotide carrier molecule comprising a target-hybridizing sequence may further include a non-target-hybridizing sequence. Specific embodiments of oligonucleotide probes comprising a non-target hybridizing sequence include, for example, probes that form conformations held by intramolecular hybridization, such as conformations generally referred to as hairpins. Particularly suitable hairpin probes include a "molecular torch" (see, e.g., U.S. Pat. Nos. 6,849,412; 6,835,542; 6,534,274; and 6,361,945, each incorporated by reference herein) and a "molecular beacon" (see, e.g., Tyagi et al., supra; U.S. Pat. Nos. 5,118,801 and 5,312,728, supra). Methods for using such hairpin probes are well-known in the art. In other embodiments, an oligonucleotide carrier molecule is a linear oligomer that does not substantially form conformations held by intramolecular bonds.

In other embodiments, the probe carrier molecule is a protein. Particularly suitable protein carrier molecules include antibodies as well as other proteins having binding specificity for another molecule such as, for example, peptides (e.g., neuropeptides, peptide hormones), peptide aptamers, antibody-binding proteins, toxins, lectins, growth factors, cytokines, enzymes, and enzyme substrates. Antibody-binding proteins may include, for example, protein A, protein G, soluble Fc receptor, protein L, anti-IgG, anti-IgA, anti-IgM, anti-IgD, anti-IgE, and fragments thereof. In some variations, a peptide carrier molecule is capable of functioning as organelle localization peptide by targeting the conjugated far-red dye for localization within a particular cellular substructure by cellular transport mechanisms. In some variations, a protein carrier molecule (e.g., an antibody, peptide, peptide aptamer, lectin) binds specifically to a cell-surface molecule; cell-surface-binding proteins such as antibodies may be used, e.g., in a variety of cell imaging and flow cytometry applications, including, e.g., microscopy, cell counting, cell sorting, and biomarker detection.

In yet other embodiments, the carrier molecule comprises a lipid (e.g., a lipid having from 6 to 25 carbons), including glycolipids, phospholipids, and sphingolipids. In some variations, the carrier molecule is a lipid assembly (e.g., a liposome) or is a lipoprotein. Some lipophilic substituents are useful for facilitating transport of the conjugated far-red dye into cells or cellular organelles.

Methods for conjugating fluorescent labels to carrier molecules, including biomolecules such as nucleic acids and proteins, to generate labeled probes are generally well-known in the art and are readily utilized by a skilled artisan in preparing far-red dye probes in accordance with the present invention.

A stabilized formulation comprising a far-red dye probe as described herein may further include one or more additional components for performing an assay utilizing the probe. For example, in some embodiments of a stabilized far-red dye probe formulation comprising an oligonucleotide carrier molecule, the formulation further contains one or more amplification oligomers for generating an amplification product specifically hybridizable by the oligonucleotide in an amplification and detection assay. In some variations, therefore, a far-red dye probe formulation comprising an oligonucleotide conjugated to a far-red dye probe further includes a first amplification oligomer, and (i) the oligonucleotide includes a target-hybridizing sequence that specifically binds to a first sequence contained within a target region of a target nucleic acid, (ii) the first amplification oligomer includes a target-hybridizing sequence that specifically binds to a second sequence contained within the target region, and (iii) the first amplification oligomer is configured to produce, in an amplification assay comprising the target nucleic acid as a template, an amplification product containing the target region. In some such embodiments, the formulation further includes a second amplification oligomer comprising a target-hybridizing sequence that specifically binds to a third sequence contained within the target region, and the first and second amplification oligomers are configured to amplify the target region in multiple cycles of the amplification assay. In some variations of a formulation further containing one or more amplification oligomers, the amplification oligomer(s) are configured to perform transcription-associated amplification of a target region; for example, in some embodiments further comprising a first amplification oligomer as described above, the first amplification oligomer is a promoter-based amplification oligomer further including a promoter sequence (e.g., a T7 promoter sequence) located 5' to the first target-hybridizing sequence. In yet other, non-mutually exclusive embodiments of a formulation further containing one or more amplification oligomers, the amplification oligomer(s) are configured to perform a distinct phase of an amplification procedure comprising two or more distinct phases (also referred to herein as a "multiphasic" nucleic acid amplification); such amplification systems are described, e.g., in U.S. Pat. No. 9,139,870 to Nelson et al., incorporated by reference herein. A formulation further containing one or more amplification oligomers as above may further include one or more additional components suitable for performing the amplification assay such as, e.g., salts, co-factors, nucleotide triphosphates (e.g., dATP, dCTP, dGTP, dTTP, ATP, CTP, GTP, UTP), and/or enzymes (e.g., reverse transcriptase and/or RNA polymerase).

In some embodiments, a stabilized far-red dye probe formulation as described herein is a concentrated preparation of an far-red dye probe (for example, an oligonucleotide far-red dye probe, optionally with one or more additional components for performing an amplification and detection assay), often useful as bulk product for use in an assay.

In typical variations, the formulation is stable over extended periods of time. For example, the formulations may be stable for at least about two weeks, at least about one month, at least about two months, at least about three months, or at least about six months. In some embodiments, the formulation is stable for at least about 12 months, at least about 18 months, at least about 24 months, or at least about 30 months.

A stabilized far-red dye probe formulation as described herein may be stored at temperatures from about −80° C. to about 40° C., from about −20° C. to about 25° C., from about 0° C. to about 25° C., from about 0° C. to about 15° C., from about 0° C. to about 10° C., or from about 2° C. to about 8° C. In various embodiments, the formulation may be stored at about 0° C., 1° C., 2° C., 3° C., 4° C., 5° C., 6° C., 7° C., 8° C., 9° C., or 10° C. Generally, the formulation is stable and retains activity at these ranges. In some variations, the formulation is stable from about −80° C. to about 25° C. or from about 4° C. to about 25° C. In more particular variations, a liquid formulation is stable at a temperature from about −80° C. to about −20° C., from about −80° C. to about 4° C., or from about −80° C. to about 25° C. In other particular variations, a lyophilized formulation is stable at a temperature from about 4° C. to about 25° C. or from about 4° C. to about 40° C. Ranges intermediate to the above recited temperatures, for example, from about 2° C. to about 18° C., are also intended to be part of this invention. For example, ranges of values using a combination of any of the above recited values as upper and/or lower limits are intended to be included.

In particular embodiments, for long-term storage, an aqueous formulation as described herein may be aliquoted into, e.g., vials, ampules, or other containers and lyophilized according to procedures known in the art. The lyophilized product typically appears as a powder or cake. The containers are then sealed; in some such variations, the seal permits later injection of diluent through the seal and into the container. Methods of preparing such stabilized, lyophilized far-red dye probe formulations from the aqueous formulation, as well as the lyophilized formulations prepared by such methods, are additional aspects of the present invention. In yet another aspect, the present invention provides a stabilized, lyophilized far-red dye probe formulation that enables reconstitution into an aqueous far-red dye probe formulation as described herein.

Methods of preparing a stabilized, aqueous far-red dye probe formulation from a lyophilized formulation as described herein are also encompassed by the present invention; such methods generally include dissolving the lyophilized far-red dye probe formulation in a suitable diluent to provide a reconstituted formulation. Suitable diluents may be readily selected by a skilled artisan depending, e.g., on the intended use of the far-red dye probe and may include, for example, water or an aqueous solution containing a buffering agent (e.g., Tris). In some embodiments, the diluent contains a stabilizing surfactant such as that contained in the stabilized, lyophilized formulation. Thus, in some variations, the diluent contains a non-linear surfactant (e.g., a polyoxyethylene sorbitan fatty acid ester or digitonin) or foamban; in some such embodiments, the stabilizing surfactant is present in the diluent at a concentraton of from about 0.06% (v/v) to about 20% (v/v), from about 0.06% (v/v) to about 10% (v/v), from about 0.06% (v/v) to about 5% (v/v), from about 0.1% (v/v) to about 20% (v/v), from about 0.1% (v/v) to about 10% (v/v), from about 0.1% (v/v) to about 5% (v/v), from about 0.5% (v/v) to about 20% (v/v), from about 0.5% (v/v) to about 10% (v/v), or from about 0.5% (v/v) to about 5% (v/v).

In a related aspect, an aqueous, stabilized far-red dye probe formulation as described herein is prepared by a method that generally includes the following steps: (a) providing a lyophilized far-red dye probe formulation that enables reconstitution into an aqueous solution comprising at least one buffering agent and a far-red dye probe comprising a far-red dye conjugated to a carrier molecule, and (b) dissolving the lyophilized far-red dye probe formulation of (a) in a diluent to provide a reconstituted formulation, where at least one of the lyophilized far-red dye probe formulation and the diluent contains a non-linear surfactant or foamban, and where the reconstituted formulation contains the non-linear surfactant or foamban at a concentration of greater than about 0.05% (v/v). In some embodiments, only the lyophilized formulation comprises the stabilizing surfactant; in some such variations, the stabilizing surfactant is present in an aqueous solution from which the lyophilized formulation is derived at a concentration of from about 0.06% (v/v) to about 20% (v/v), from about 0.06% (v/v) to about 10% (v/v), from about 0.1% (v/v) to about 20% (v/v), from about 0.1% (v/v) to about 10% (v/v), from about 0.5% (v/v) to about 20% (v/v), from about 0.5% (v/v) to about 10% (v/v), from about 1% (v/v) to about 20% (v/v), or from about 1% (v/v) to about 10% (v/v). In other embodiments, only the diluent comprises the stabilizing surfactant; in some such variations, the stabilizing surfactant is present in the diluent at a concentration of from about 0.06% (v/v) to about 20% (v/v), from about 0.06% (v/v) to about 10% (v/v), from about 0.1% (v/v) to about 20% (v/v), from about 0.1% (v/v) to about 10% (v/v), from about 0.5% (v/v) to about 20% (v/v), from about 0.5% (v/v) to about 10% (v/v), from about 1% (v/v) to about 20% (v/v), or from about 1% (v/v) to about 10% (v/v). In yet other embodiments, both the lyophilized far-red dye probe formulation and the diluent contain the non-linear surfactant or foamban; in some such variations, the stabilizing surfactant is present in the lyophilized formulation and the diluent at concentrations configured to produce, upon reconstitution of the lyophilized formulation in the diluent, a final surfactant concentration of from about 0.06% (v/v) to about 20% (v/v), from about 0.06% (v/v) to about 10% (v/v), from about 0.1% (v/v) to about 20% (v/v), from about 0.1% (v/v) to about 10% (v/v), from about 0.5% (v/v) to about 20% (v/v), from about 0.5% (v/v) to about 10% (v/v), from about 1% (v/v) to about 20% (v/v), or from about 1% (v/v) to about 10% (v/v). A method as above may further include preparing the lyophilized far-red dye probe formulation by lyophilizing an aqueous solution comprising the far-red dye probe and the at least one buffering agent.

In certain aspects of the present invention, a container containing a stabilized, lyophilized far-red dye probe formulation as described herein is provided in a kit with a second container containing a diluent. The diluent may contain a non-linear surfactant or foamban such as discussed above with respect to preparing a reconstituted formulation from the lyophilized formulation. A far-red dye probe formulation and diluent may be packaged in a variety of different embodiments, and those skilled in the art will appreciate that the invention embraces many different kit configurations. For example, for embodiments in which the far-red dye probe comprises an oligonucleotide carrier molecule containing a target-hybridizing sequence that specifically binds to a nucleic acid target region, a kit may further include a third container containing one or more amplification oligomers for amplifying the target region. In some such variations in which the far-red dye probe formulation comprises an amplification oligomer that specifically binds to the target region, the third container may include a second amplification oligomer that specifically binds to the target region and which are configured to produce, in an amplification assay, an amplification product containing the target region; such kits embodiments may be used, for example, for multiphasic amplification systems such as described, e.g., in U.S. Pat. No. 9,139,870 to Nelson et al., incorporated by reference herein. A kit comprising an oligonucleotide far-red dye probe for use in an amplification and detection assay may contain other reagents suitable for performing in vitro amplification such as, e.g., buffers, salt solutions, appropriate nucleotide triphosphates (e.g., dATP, dCTP, dGTP, dTTP, ATP, CTP, GTP, UTP), and/or enzymes (e.g., reverse transcriptase, and/or RNA polymerase). In certain embodiments, the kit further includes a set of instructions for practicing methods in accordance with the present invention, where the instructions may be associated with a package insert and/or the packaging of the kit or the components thereof.

In a related aspect, the present invention provides a kit comprising (i) a first sealed container containing a lyophilized far-red dye probe formulation that enables reconstitution into an aqueous solution comprising at least one buffering agent and a far-red dye probe comprising a far-red dye conjugated to a carrier molecule, and (ii) a second sealed container containing a diluent, where at least one of the lyophilized far-red dye probe formulation and the diluent comprises a non-linear surfactant or foamban, and where reconstitution of the lyophilized far-red dye probe formulation in the diluent provides a final concentration of the non-linear surfactant or foamban of greater than about 0.05% (v/v). In some embodiments, only the lyophilized formulation comprises the stabilizing surfactant; in some such variations, the stabilizing surfactant is present in an aqueous solution from which the lyophilized formulation is derived at a concentration of from about 0.06% (v/v) to about 20% (v/v), from about 0.06% (v/v) to about 10% (v/v), from about 0.1% (v/v) to about 20% (v/v), from about 0.1% (v/v) to about 10% (v/v), from about 0.5% (v/v) to about 20% (v/v), from about 0.5% (v/v) to about 10% (v/v), from about 1% (v/v) to about 20% (v/v), or from about 1% (v/v) to about 10% (v/v). In other embodiments, only the diluent comprises the stabilizing surfactant; in some such variations, the stabilizing surfactant is present in the diluent at a concentration of from about 0.06% (v/v) to about 20% (v/v), from about 0.06% (v/v) to about 10% (v/v), from about 0.1% (v/v) to about 20% (v/v), from about 0.1% (v/v) to about 10% (v/v), from about 0.5% (v/v) to about 20% (v/v), from about 0.5% (v/v) to about 10% (v/v), from about 1% (v/v) to about 20% (v/v), or from about 1% (v/v) to about 10% (v/v). In yet other embodiments, both the lyophilized far-red dye probe formulation and the diluent contain the non-linear surfactant or foamban; in some such variations, the stabilizing surfactant is present in the lyophilized formulation and the diluent at concentrations configured to produce, upon reconstitution of the lyophilized formulation in the diluent, a final surfactant concentration of from about 0.06% (v/v) to about 20% (v/v), from about 0.06% (v/v) to about 10% (v/v), from about 0.1% (v/v) to about 20% (v/v), from about 0.1% (v/v) to about 10% (v/v), from about 0.5% (v/v) to about 20% (v/v), from about 0.5% (v/v) to about 10% (v/v), from about 1% (v/v) to about 20% (v/v), or from about 1% (v/v) to about 10% (v/v). As noted previously, a far-red dye probe formulation and diluent may be packaged in a variety of different embodiments, and those skilled in the art will appreciate that the invention embraces many different kit configurations.

In yet another aspect, the present invention provides a diagnostic product comprising a sealed container containing a stabilized far-red dye probe formulation as set forth above. In some variations, the stabilized far-red dye formulation is a lyophilized formulation as described herein.

The invention is further illustrated by the following non-limiting examples.

EXAMPLES

Unless otherwise specified, reagents commonly used in the RT-TMA-based assays described herein include the following. Target Capture Reagent (TCR) formulation: 250 mM HEPES, 1.88 M LiCl, 310 mM LiOH, 100 mM EDTA, pH 6.4, and 250 μg/ml of paramagnetic particles (0.7-1.05 micron particles, Sera-Mag™ MG-CM) with $(dT)_{14}$ oligomers (SEQ ID NO:20) covalently bound thereto. Wash Solution formulation: 10 mM HEPES, 150 mM NaCl, 6.5 mM NaOH, 1 mM EDTA, 0.3% (v/v) ethanol, 0.02% (w/v) methylparaben, 0.01% (w/v) propylparaben, and 0.1% (w/v) sodium lauryl sulfate, pH 7.5. Amplification Reagent & Promoter Reagent formulations: 11.61 mM Tris base, 14.94 mM Tris-HCl, 28.5 mM $MgCl_2$, 23.30 mM KCl, 3.3% Glycerol, 0.02% PRO CLIN 300, 0.05 mM Zinc Acetate Dihydrate, 0.76 mM each of dATP, dCTP, dGTP, and dTTP, 6.50 mM each ATP, CTP, and GTP, 7.50 mM UTP, to which primers are added. Enzymes Reagent formulation: 57.46 mM HEPES, 49.58 mM N-Acetyl-L-Cysteine, 0.98 mM EDTA free acid, 0.039 mM EDTA Disodium Dihydrate, 0.10 v/v TRITON X-100, 49.61 mM KCl, 0.20 v/v Glycerol, 0.03 w/v Trehalose Dihydrate, MMLV reverse transcriptase (RT) and T7 RNA polymerase.

Amplification and detection reactions were performed using a Stratagene Mx3000 in a biphasic real-time TMA format. Briefly, samples were incubated with 100 μl TCR, containing target capture oligomers (SEQ ID NOs:1, 7, 11, & 16, each at 15 pmol/rxn) and T7 primers (SEQ ID NOs:3, 4, 9, 13, & 18, each at 5 pmol/rxn) at 62° C. for 30 minutes, then ramped down to room temperature for 20 minutes in order to form hybridization complexes (magnetic bead- $dT_{14}$: target capture oligomer: target nucleic acid: T7 primer). The hybridization complexes were washed and eluted into the Amplification Reagent, containing non-T7 primers (SEQ ID NOs:2, 8, 12, & 17 each at 15 pmol/rxn). Samples were incubated at 43° C. during addition of Enzyme Reagent (25 µl) and subsequent addition of Promoter Reagent (25 µl). The Promoter Reagent contained the T7 primers (SEQ ID NOs:3, 4, 9, 13, & 18 each at 15 pmol/rxn) and the Torch oligos (SEQ ID NOs:5, 6, 10, 14, 15, & 19, each at 15 pmol/rxn). Fluorescence emission, reflecting Torch binding to target amplicon and resulting in dye separation from quencher, was measured in real-time on the Stratagene instrument every 30 seconds for 1 hour. Fluorescence curve profiles were analyzed for amplification of target. See e.g., U.S. Pat. No. 9,139,870 B2. Target nucleic acids for each condition were either lysates from *Lactobacillus* crispatus, *Gardnerella vaginalis, Eggerthella lenta*, or were an in vitro transcript comprising at least the sequences for hybridizing with the target capture oligomer, T7 primers, non-T7 primers and torches for a target to perform the capture, amplification and detection reactions. (Bacterial strains for preparing lysates were purchased from ATCC, Manassas, VA, cat. nos. ATCC 33820, ATCC 14018, & ATCC 25559).

Example 1

Several experiments were performed that showed a 25-70% drop in CY5.5® RFU signal seen after a 30 day incubation of a CY5.5® dye containing solution. The incubated CY5.5® dye containing solution was used in a real time (RT) TMA assay, as generally described above. The CY5.5® dye in this example was attached to a torch oligonucleotide for detection of an internal control target nucleic acid. Some representative data are shown below in Table 1 illustrating a drop of 35% with the internal control CY5.5® torch while the FAM, HEX and ROX torches dropped only about 10% following the 30 day incubation. Additional studies were tried with different far red dyes as well as alternative buffer formulations, and similar drops in signal were seen over time. Stored far-red dye containing reagents showing a significant decrease in RFU signal become unusable because the unreliable signal provides invalid assay results. As such, it is not recommended to store far-red dye containing solutions for later use in an assay that utilizes the RFU signal from these dyes, but instead that unused portions are discarded.

TABLE 1

Real-time TMA 4-plex amplification and detection assay results using a far-red dye containing solution following a 30 day incubation

| Fluorophore | Target | Time Point | N | RFURange Mean | T Time Normalized Mean | % Drop (RFU) |
|---|---|---|---|---|---|---|
| CY5.5 ® | Internal | 0 | 10 | 2,161 | 15.9 | 35% |
| | control | 38 | 10 | 1,550 | 15.7 | |
| FAM | Lcrisp | 0 | 5 | 7,870 | 14.9 | 7% |
| | 1e6 cfu/mL | 38 | 5 | 7,955 | 14.7 | |
| HEX | Gvag | 0 | 5 | 6,805 | 18.5 | 10% |
| | 1e6 cfu/mL | 38 | 5 | 7,057 | 18.5 | |
| ROX | Egg | 0 | 5 | 6,196 | 9.6 | 15% |
| | 1e10 c/mL | 38 | 5 | 7,253 | 8.9 | |

A CY5.5® dye containing solution was incubated for 30 days, as described above. Prior to using the stored solution in a real-time amplification and detection reaction, part of the CY5.5® dye containing solution was heated to 80° C. for 10 minutes, while another part was not. Each CY5.5® dye containing condition was then used for an amplification and detection reaction and the results are presented in Table 2. These results show that the 80° C./10 minute heat step fully restored the loss in CY5.5® RFU signal compared to the unheated control. This illustrates that the far-red dye signal loss in an incubated solution is not due to degradation of the dye but points to a micelle formation where the CY5.5® fluorophores come in close proximity to and quench each other.

TABLE 2

Real-time TMA 4-plex amplification and detection assay results using a far-red dye containing solution following a 30 day incubation and an 80° C./10 minute heat step

| Fluorophore | Target | Sample Type | RFU Range N | RFU Range Mean | TTime_ Norm Mean | % Diff RFU | % Diff T Time |
|---|---|---|---|---|---|---|---|
| FAM | Lcrisp | CONTROL | 5 | 8984 | 14.43 | 6% | −1% |
| | 1e6 cfu/mL | HEATED 80° C. FOR 10 MIN | 5 | 8406 | 14.57 | | |
| HEX | Gvag | CONTROL | 5 | 7753 | 18.51 | 0% | 6% |
| | 1e6 cfu/mL | HEATED 80° C. FOR 10 MIN | 5 | 7746 | 17.33 | | |
| ROX | Egg | CONTROL | 5 | 7297 | 9.10 | −1% | 0% |
| | 1e10 c/mL | HEATED 80° C. FOR 10 MIN | 5 | 7385 | 9.06 | | |
| CY5.5 ® | Internal control | CONTROL | 35 | 806 | NA | −224% | NA |
| | | HEATED 80° C. FOR 10 MIN | 35 | 2608 | 16.84 | | |

NA = No detectable signal, thus no TTime available.

In order to break up the micelle formation that occurs over time, 30 day storage measurements were repeated for far-red dye containing solutions that further contained a non-ionic surfactant. In this experiment, TRITON™ X-100 or TWEEN® 20 (Millipore Sigma, St. Louis, MO, cat. nos. 93443 & P1379) were used as the non-ionic surfactant. The far-red dye containing solution was a Promoter Reagent, as described above, containing a CY5.5® labeled molecular torch and either TRITON X-100 or TWEEN 20 at varying concentrations. The solutions were stored for 38 days or 40 days and then used in a real-time isothermal amplification and detection reaction. Results are shown in Table 3 and Table 4

The addition of TRITON™ X-100 to the Promoter Reagent resulted in more than a 70% drop in CY5.5® RFU signal between 0 days and 40 days of storage as compared to the control condition without TRITON X-100 which dropped by 23% (see Table 3).

TABLE 3

Comparing 40 day incubation to 0 day incubation of a Promoter Reagent containing a CY5.5 ® component and different concentrations of TRITON X-100.

| Fluorophore | Target | Concentration Triton X-100% v/v | Time Point N | Day 0 RFU Mean | Day 40 RFU Mean | % Diff |
|---|---|---|---|---|---|---|
| FAM | Lcrisp | 0 | 5 | 7,901 | 8,887 | 12% |
| | 1e6 cfu/mL | 1 | 5 | 8,438 | 8,781 | 4% |
| | | 10 | 5 | 9,132 | 9,763 | 7% |
| | | 20 | 5 | 9,021 | 9,291 | 3% |
| HEX | Gvag | 0 | 5 | 7,012 | 7,881 | 12% |
| | 1e6 cfu/mL | 1 | 5 | 7,721 | 8,585 | 11% |
| | | 10 | 5 | 7,614 | 7,857 | 3% |
| | | 20 | 5 | 7,765 | 8,973 | 16% |
| ROX | Egg | 0 | 5 | 6,535 | 7,373 | 13% |
| | 1e10 c/mL | 1 | 5 | 7,289 | 7,697 | 6% |
| | | 10 | 5 | 7,996 | 8,212 | 3% |
| | | 20 | 5 | 7,828 | 8,398 | 7% |
| CY5.5 ® | Internal | 0 | 35 | 2,686 | 2,063 | −23% |
| | control | 1 | 35 | 4,408 | 1,557 | −65% |
| | | 10 | 35 | 4,781 | 1,126 | −76% |
| | | 20 | 35 | 4,974 | 1,283 | −74% |

The addition of TWEEN 20 to the Promoter Reagent resulted in a minimal drop in CY5.5® RFU signal between 0 days and 38 days of storage as compared to the control condition without TWEEN 20, which dropped by 29%. As shown in Table 4, at 1% to 20% of TWEEN 20 only a 4.6% to 10.4% drop in CY5.5® RFU signal was seen between day 0 and day 38 compared to the control condition (i.e., no TWEEN 20 added), which dropped 29% between days 0 and 38.

TABLE 4

Comparing 38 day to 0 day incubation of a Promoter Reagent containing a CY5.5 ® component and different concentrations of TWEEN 20

| | | | RFU Mean | | | T Time Mean | | |
|---|---|---|---|---|---|---|---|---|
| Fluorophore | Target | Condition | Day 0 | Day 38 | % Diff | Day 0 | Day 38 | % Diff |
| FAM | Lcrisp | 1% TWEEN 20 | 9,183 | 8,766 | 4.5% | 14.3 | 14.4 | −0.9% |
| | 1e6 | 10% TWEEN 20 | 9,898 | 10,312 | −4.2% | 12.7 | 12.7 | −0.2% |
| | cfu/mL | 20% TWEEN 20 | 10,481 | 10,057 | 4.0% | 11.7 | 11.9 | −1.6% |
| | | CONTROL | 8,618 | 8,942 | −3.8% | 14.2 | 14.3 | −0.8% |
| HEX | Gvag | 1% TWEEN 20 | 7,758 | 8,258 | −6.5% | 17.9 | 18.5 | −3.4% |
| | 1e6 | 10% TWEEN 20 | 9,153 | 9,364 | −2.3% | 15.9 | 16.9 | −6.2% |
| | cfu/mL | 20% TWEEN 20 | 9,282 | 9,910 | −6.8% | 14.8 | 15.6 | −5.5% |
| | | CONTROL | 7,830 | 7,360 | 6.0% | 17.7 | 18.4 | −4.1% |
| ROX | Egg | 1% TWEEN 20 | 7,721 | 7,307 | 5.4% | 9.0 | 9.0 | −0.2% |
| | 1e10 c/mL | 10% TWEEN 20 | 7,453 | 8,337 | −11.9% | 7.9 | 7.9 | 0.3% |
| | | 20% TWEEN 20 | 8,917 | 8,313 | 6.8% | 7.3 | 7.4 | −0.9% |
| | | CONTROL | 7,394 | 7,452 | −0.8% | 9.1 | 9.0 | 1.2% |
| CY5.5 ® | Internal | 1% TWEEN 20 | 4,676 | 4,462 | 4.6% | 16.4 | 17.0 | −3.2% |
| | control | 10% TWEEN 20 | 5,158 | 4,887 | 5.3% | 15.0 | 14.9 | 0.8% |
| | | 20% TWEEN 20 | 5,440 | 4,873 | 10.4% | 14.3 | 14.3 | 0.6% |
| | | CONTROL | 2,404 | 1,704 | 29.1% | 16.1 | 15.5 | 3.8% |

TWEEN 20 concentrations at and below 1% were added to a number of Promoter Reagents and tested in an amplification and detection reaction as described above. Promoter Reagent for use in an amplification and detection of a target nucleic acid were prepared to include a CY5.5® labeled torch oligonucleotide, and also include 1% TWEEN 20, 0.03% TWEEN 20, or 0.001% TWEEN 20. The various Promoter Reagent conditions were then used in real-time isothermal amplification and detection reactions on day 0 and after a 42 day storage (day 42). Results are shown in Table 5. The drop in CY5.5® RFU signal from day 0 to day 42 was more pronounced with the conditions wherein the Promoter Reagent contained a lower concentration of TWEEN 20.

TABLE 5

Comparing 42 day to 0 day incubation of a Promoter Reagent containing CY5.5 ® and different concentrations of Tween 20

| | | | RFU Mean | | | T Time Mean | | |
|---|---|---|---|---|---|---|---|---|
| Fluorophore | Target | Condition | Day 0 | Day 42 | % Diff | Day 0 | Day 42 | % Diff |
| CY5.5 ® | Internal control | 1% TWEEN 20 | 4,134 | 3,625 | 12.30% | 15.5 | 15.5 | 0.40% |
| | | 0.03% TWEEN 20 | 4,124 | 2,876 | 30.30% | 15.7 | 15.2 | 3.10% |
| | | 0.001% TWEEN 20 | 3,211 | 1,118 | 65.20% | 15.2 | 14.4 | 5.30% |

In a further experiment other surfactants were added to far-red dye containing solutions. Promoter Reagents were prepared for use in an amplification and detection reaction. The Promoter Reagent containing a CY5.5® torch was prepared in a bulk solution. The bulk solution was then separated into a number of conditions wherein each of the conditions contained one of the following surfactants (at 1% v/v): TWEEN® 40 (Millipore Sigma, cat. no. P1504), TWEEN® 60 (Millipore Sigma, cat. no. P1629), Synperonic (Millipore Sigma, cat. no. 7579), Foamban (Munzing, cat. no. MS-575), and Digitonin (Millipore Sigma, cat. no. D141). Each conditions was then used in real-time isothermal amplification and detection reactions on day 0, after 17 days of storage (day 17), and after a 38 day storage (day 38). As shown in Table 6, TWEEN 40, TWEEN 60, Foamban and Digitonin resulted in minimal drop in CY5.5® RFU signal between 0 days and 38 days of storage. Synperonic did not reduce the CY5.5® RFU signal drop. Synperonic, like TRITON X-100, has a linear structure, which may render these surfactants less efficient in disrupting micelle formation of the far-red dye molecules. The TWEENs as well as Digitonin have branched structures which should lead to more disorder and thus less conducive to micelle formation.

TABLE 6

Comparing CY5.5 ® RFU signal after 38 day, 17, day, and 0 day storage in the presence of a number of different surfactants

| | Time Point | | RFU Range | | T Time | | T Slope | | % Difference (38 days compared to baseline) | | |
|---|---|---|---|---|---|---|---|---|---|---|---|
| Surfactant | (days) | N | Mean | % CV | Mean | % CV | Mean | % CV | RFU | T Time | T Slope |
| TWEEN 20 | 0 | 30 | 5,199 | 7.04 | 15.1 | 2.59 | 0.17 | 5.29 | −7.5% | −4.1% | −7.2% |
| | 17 | 30 | 5,251 | 10.49 | 15.1 | 3.47 | 0.16 | 3.61 | | | |
| | 38 | 30 | 4,808 | 11.53 | 14.5 | 3.44 | 0.16 | 5.92 | | | |
| TWEEN 40 | 0 | 30 | 4,886 | 7.82 | 15.2 | 4.36 | 0.17 | 5.23 | −1.2% | −3.3% | −3.5% |
| | 17 | 30 | 5,106 | 9.03 | 15.5 | 3.92 | 0.17 | 4.38 | | | |
| | 38 | 30 | 4,829 | 15.69 | 14.7 | 4.36 | 0.17 | 4.46 | | | |
| TWEEN 60 | 0 | 30 | 4,854 | 8.24 | 15.1 | 2.83 | 0.17 | 3.81 | −0.1% | −2.1% | −3.8% |
| | 17 | 30 | 5,127 | 10.90 | 15.3 | 3.23 | 0.17 | 5.50 | | | |
| | 38 | 30 | 4,848 | 10.84 | 14.7 | 4.07 | 0.17 | 4.60 | | | |
| FOAMBAN | 0 | 30 | 4,708 | 7.02 | 16.4 | 2.72 | 0.16 | 5.30 | −10.6% | −6.3% | 4.1% |
| | 17 | 30 | 4,371 | 9.94 | 16.2 | 2.33 | 0.16 | 4.40 | | | |
| | 38 | 30 | 4,208 | 9.65 | 15.3 | 3.12 | 0.17 | 4.39 | | | |
| DIGITONIN | 0 | 30 | 5,117 | 8.09 | 15.5 | 3.31 | 0.17 | 3.92 | −2.7% | −3.3% | −4.0% |
| | 17 | 30 | 5,307 | 11.49 | 15.7 | 3.18 | 0.16 | 4.59 | | | |
| | 38 | 30 | 4,980 | 10.77 | 15.0 | 3.93 | 0.16 | 3.96 | | | |
| SYNPERONIC | 0 | 30 | 4,964 | 8.45 | 15.2 | 2.52 | 0.17 | 5.75 | −38.4% | −7.2% | −3.5% |
| | 17 | 30 | 4,297 | 8.39 | 14.7 | 3.62 | 0.17 | 5.51 | | | |
| | 38 | 30 | 3,057 | 21.79 | 14.1 | 4.02 | 0.17 | 5.80 | | | |

Structures of additional Digitonin and Synperonic surfactants are shown below.

Digitonin:

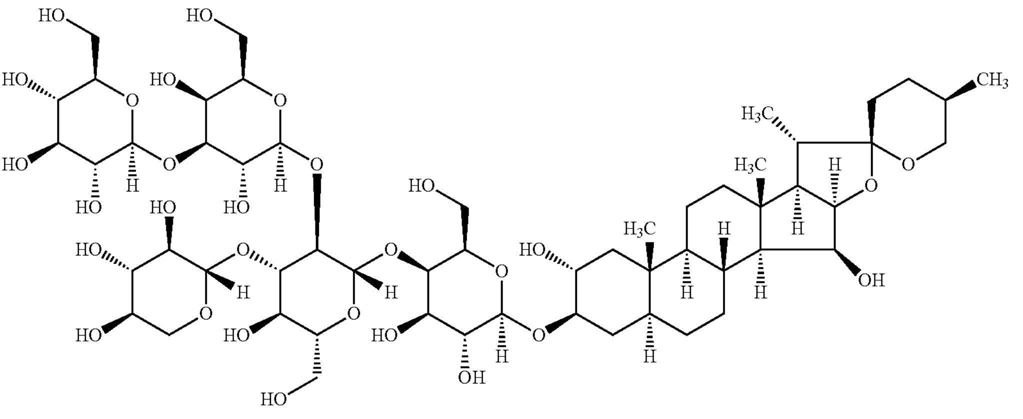

Synperonic F108:

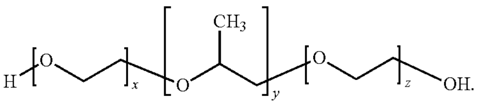

A number of solutions containing a far-red dye and surfactant were prepared and lyophilized. The lyophilized compositions were then reconstituted with a diluent also containing a surfactant. The reconstituted solutions were then used in real-time amplification and detection assays. In one configuration, a Promoter Reagent, as described above, was prepared to contain a CY5.5® labeled torch and TWEEN-20, as shown in Table 7. Physical characteristics of the lyophilized pellets were evaluated, and those with acceptable characteristics were then reconstituted with a diluent containing 1% TWEEN-20 to provide solutions containing from 1.41% TWEEN-20 to 2.24% TWEEN-20 in the reconstituted Promoter Reagent. The reconstituted Promoter Reagents were then used in real-time amplification and detection assays at days 0 and 30, and robust CY5.5® RFU signals were obtained without significant drop between days 0 and 30. Poor physical characteristics that were observed following a lyophilization cycle included: pre-lyophilization solution containing an excess of surfactant would not fully lyophilize (remained partially in a liquid form); and pre-lyophilization solutions containing too little of surfactant showed blue dots (indicating micelle formation of the far-red dye components). Thus, depending on the formulation of the far-red dye containing solution, the surfactant concentration in a pre-lyophilized solution is only required to be the minimum amount to prevent micelle formation during a short incubation period prior to lyophilization. The remainder of the surfactant needed to provide longer term incubation protection of the far-red dye component is then provided using a surfactant containing reconstitution solution (diluent).

TABLE 7

TWEEN-20 in lyophilized Promoter Reagents and in diluent reagents

| % TWEEN-20 in Promoter Reagent (pre-lyophilization) | % TWEEN-20 in reconstituted Promoter Reagent |
|---|---|
| 3.0% TWEEN-20 | 2.24% TWEEN-20 |
| 1.5% TWEEN-20 | 1.62% TWEEN-20 |
| 1.0% TWEEN-20 | 1.41% TWEEN-20 |

TABLE 8

Exemplary Sequences

| Condition | SEQ ID NO: | Sequence (5′ to 3′)† | Seq Type |
|---|---|---|---|
| *L. crispatus* | 1 | ucuguuaguuccTTTAAAAAAAAAAAA AAAAAAAAAAAAAAAAA | Target capture oligomer |
| | 2 | CGGATGGGTGAGTAAC | Non-T7 primer |
| | 3 | aatttaatacgactcactatagggaga TAAGCCCTTACCTTACCA | T7 primer |
| | 4 | aatttaatacgactcactatagggaga TAAGCCGTTACCTTACCA | T7 primer |
| | 5 | gucugggauaccacuuggaaa-cagac | Torch |
| | 6 | cacuc-acgcaugucuagagug | Torch |
| *G. vaginalis* | 7 | caugcuccgccgcuuguTTTAAAAAAA AAAAAAAAAAAAAAAAAAAAAA | Target capture oligomer |
| | 8 | CTTACCTGGGCTTGACATGTGCCTG | Non-T7 primer |

TABLE 8-continued

Exemplary Sequences

| Condition | SEQ ID NO: | Sequence (5′ to 3′)† | Seq Type |
|---|---|---|---|
| | 9 | aatttaatacgactcactatagggaga CACCACCTGTGAACCTGC | T7 primer |
| | 10 | ccugcagagauguggguuuc-gcagg | Torch |
| *Eggerthella* | 11 | guaccgucgaugucuucccugTTTAAA AAAAAAAAAAAAAAAAAAAAAAAAAA | Target capture oligomer |
| | 12 | AGCGTTATCCGGATTC | Non-T7 primer |
| | 13 | aatttaatacgactcactatagggaga TTCGGAACCCGGCTCGAGCTTAAG | T7 primer |
| | 14 | ccgcu-caggcgguugcucaagcgg | Torch |
| | 15 | ccgcu-caggcgguugcucaagcgg | Torch |
| Internal Control | 16 | cguucacuauuggucucugcauucTTT AAAAAAAAAAAAAAAAAAAAAAAAAA AAA | Target capture oligomer |
| | 17 | GATTATATAGGACGACAAG | Non-T7 primer |
| | 18 | aatttaatacgactcactatagggaga GATGATTGACTTGTGATTCCGC | T7 primer |
| | 19 | gcaug-gugcgaauugggacaugc | Torch |
| | 20 | TTTTTTTTTTTTTT | (dT)14 |

†Upper case letteres in the target capture oligomers represent the capture tail while lower case letter represent the target specific sequences.
The 27 nucleotides on the 5′ end of the T7 primers (all in lowercase letters) represent a T7 promoter sequence while the remainder of the sequences (all in uppercase letters) are target hybridizing sequences.
Torches comprise both dye and quencher molecules, one on each of their 5′ and 3′ ends, and a non-nucleotide linker arm as indicated by "-" in the sequence.

Exemplary Embodiments

Embodiment 1. A stabilized far-red dye probe formulation comprising:

a far-red dye probe comprising a far-red dye conjugated to a carrier molecule;

a non-linear surfactant at a concentration of greater than about 0.05% (v/v); and at least one buffering agent;

wherein the formulation is an aqueous solution.

Embodiment 2. The formulation of Embodiment 1, wherein the far-red dye is a far-red cyanine dye.

Embodiment 3. The formulation of Embodiment 2, wherein the far-red cyanine dye is selected from the group consisting of cyanine 5 and cyanine 5.5.

Embodiment 4. The formulation of any of Embodiments 1 to 3, wherein the non-linear surfactant is selected from the group consisting of a polyoxyethylene sorbitan fatty acid ester and digitonin.

Embodiment 5. The formulation of Embodiment 4, wherein the non-linear surfactant is the polyoxyethylene sorbitan fatty acid ester.

Embodiment 6. The formulation of Embodiment 5, wherein the polyoxyethylene sorbitan fatty acid ester is selected from the group consisting of polysorbate 20, polysorbate 40, and polysorbate 60.

Embodiment 7. The formulation of any of Embodiments 1 to 6, wherein the non-linear surfactant concentration is from about 0.06% (v/v) to about 20% (v/v), from about 0.06% (v/v) to about 10% (v/v), from about 0.1% (v/v) to about 20% (v/v), or from about 0.1% (v/v) to about 10% (v/v).

Embodiment 8. The formulation of any of Embodiments 1 to 6, wherein the non-linear surfactant concentration is from about 0.5% (v/v) to about 20% (v/v), from about 0.5% (v/v) to about 10% (v/v), from about 1% (v/v) to about 20% (v/v), or from about 1% (v/v) to about 10% (v/v).

Embodiment 9. The formulation of any one of Embodiments 1 to 8, wherein the at least one buffering agent is Tris.

Embodiment 10. The formulation of Embodiment 9, wherein the Tris buffering agent is present at a concentration of from about 5 mM to about 50 mM.

Embodiment 11. The formulation of any of Embodiments 1 to 10, wherein the carrier molecule is a nucleic acid.

Embodiment 12. The formulation of Embodiment 11, wherein the nucleic acid carrier molecule is an RNA.

Embodiment 13. The formulation of any of Embodiments 1 to 10, wherein the far-red dye probe further comprises a quencher.

Embodiment 14. The formulation of Embodiment 13, wherein the far-red dye probe is selected from the group consisting of a molecular torch, a molecular beacon, and a TaqMan probe.

Embodiment 15. The formulation of any of Embodiments 10 to 14, further comprising a first amplification oligomer, wherein the far-red dye probe comprises a target-hybridizing sequence that specifically binds to a first sequence contained within a target region of a target nucleic acid, wherein the first amplification oligomer comprises a target-hybridizing sequence that specifically binds to a second sequence contained within said target region, and wherein the first amplification oligomer is configured to produce, in an amplification assay comprising the target nucleic acid as a template, an amplification product containing said target region.

Embodiment 16. The formulation of Embodiment 15, further comprising a second amplification oligomer, wherein the second amplification oligomer comprises a target-hybridizing sequence that specifically binds to a third sequence contained within said target region, and wherein the first and second amplification oligomers are configured to amplify said target region in multiple cycles of the amplification assay.

Embodiment 17. The formulation of Embodiment 15 or 16, wherein the first amplification oligomer is a promoter-based amplification oligomer further comprising a promoter sequence located 5' to the first target-hybridizing sequence.

Embodiment 18. The formulation of any of Embodiments 15 to 17, further comprising one or more nucleotide triphosphates suitable for performing said amplification assay.

Embodiment 19. The formulation of any of Embodiments 15 to 18, further comprising one or more salts or co-factors suitable for performing said amplification assay.

Embodiment 20. A stabilized far-red dye probe formulation comprising:

a far-red dye probe comprising a far-red dye conjugated to a carrier molecule;

foamban at a concentration of greater than about 0.05% (v/v); and at least one buffering agent;

wherein the formulation is an aqueous solution.

Embodiment 21. A method of preparing a stabilized, lyophilized far-red dye probe formulation, the method comprising:

providing a formulation as in any of Embodiments 1 to 20; and lyophilizing the aqueous solution to form the lyophilized far-red dye probe formulation.

Embodiment 22. A stabilized, lyophilized far-red dye probe formulation prepared by the method of Embodiment 21.

Embodiment 23. A stabilized, lyophilized far-red dye probe formulation that enables reconstitution into an aqueous formulation as in any of Embodiments 1 to 20.

Embodiment 24. A method of preparing an stabilized, aqueous far-red dye probe formulation, the method comprising:

(a) providing a lyophilized far-red dye probe formulation as in Embodiment 22 or 23; and (b) dissolving the lyophilized far-red dye probe formulation in a diluent to provide a reconstituted formulation.

Embodiment 25. A kit comprising:

a first sealed container containing a lyophilized far-red dye probe formulation as in Embodiment 22 or 23; and a second sealed container containing a diluent.

Embodiment 26. The kit of Embodiment 25, wherein the diluent comprises the non-linear surfactant.

Embodiment 27. A method of preparing a stabilized, aqueous far-red dye probe formulation, the method comprising:

(a) providing a lyophilized far-red dye probe formulation that enables reconstitution into an aqueous solution comprising at least one buffering agent and a far-red dye probe comprising a far-red dye conjugated to a carrier molecule; and (b) dissolving the lyophilized far-red dye probe formulation in a diluent to provide a reconstituted formulation;

wherein at least one of the lyophilized far-red dye probe formulation and the diluent comprises a non-linear surfactant, and wherein the reconstituted formulation comprises the non-linear surfactant at a concentration of greater than about 0.05% (v/v).

Embodiment 28. The method of Embodiment 27, wherein both the lyophilized far-red dye probe formulation and the diluent comprise the non-linear surfactant.

Embodiment 29. The method of Embodiment 27 or 28, further comprising preparing the lyophilized far-red dye probe formulation by lyophilizing an aqueous solution comprising the far-red dye probe and the at least one buffering agent.

Embodiment 30. A kit comprising:

a first sealed container containing a lyophilized far-red dye probe formulation that enables reconstitution into an aqueous solution comprising at least one buffering agent and a far-red dye probe comprising a far-red dye conjugated to a carrier molecule; and a second sealed container containing a diluent;

wherein at least one of the lyophilized far-red dye probe formulation and the diluent comprises a non-linear surfactant, and wherein reconstitution of the lyophilized far-red dye probe formulation in the diluent provides a final non-linear surfactant concentration of greater than about 0.05% (v/v).

Embodiment 31. The kit of Embodiment 30, wherein both the lyophilized far-red dye formulation and the diluent comprise the non-linear surfactant.

Embodiment 32. A diagnostic product comprising a sealed container containing a stabilized far-red dye probe formulation as in any of Embodiments 1-20, 22, and 23.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A kit comprising:

(a) a first sealed container containing a lyophilized far-red dye probe formulation, wherein the lyophilized far-red dye probe formulation comprises a far-red dye probe comprising a far-red dye conjugated to a carrier molecule, wherein the far-red dye is a far-red cyanine dye and the carrier molecule is an RNA;

a non-linear surfactant; and at least one buffering agent;

and (b) a second sealed container containing a diluent, wherein the diluent comprises the non-linear surfactant at a concentration of from 1% (v/v) to about 5% (v/v);

wherein the non-linear surfactant is present in the lyophilized far-red dye probe formulation and the diluent at concentrations configured to produce, upon reconstitution of the lyophilized formulation in the diluent, a final non-linear surfactant concentration of from about 1% (v/v) to about 10% (v/v).

2. The kit of claim 1, wherein the far-red cyanine dye is selected from the group consisting of cyanine 5 and cyanine 5.5.

3. The kit of claim 1, wherein the non-linear surfactant is selected from the group consisting of a polyoxyethylene sorbitan fatty acid ester and digitonin.

4. The kit of claim 1, wherein the non-linear surfactant is a polyoxyethylene sorbitan fatty acid ester selected from the group consisting of polysorbate 20, polysorbate 40, and polysorbate 60.

5. The kit of claim 1, wherein the non-linear surfactant is polysorbate 20.

6. The kit of claim 1, wherein the at least one buffering agent comprises Tris.

7. The kit of claim 1, wherein the far-red dye probe further comprises a quencher.

8. The kit of claim 1, wherein the far-red dye probe is selected from the group consisting of a molecular torch and a molecular beacon.

9. The kit of claim 1, wherein the lyophilized far-red dye probe formulation further comprises a promoter-based amplification oligomer.

10. The kit of claim 5, wherein the non-linear surfactant concentration in the diluent is 1% (v/v).

11. The kit of claim 10, wherein the non-linear surfactant is present in the lyophilized far-red dye probe formulation at a concentration configured to produce, upon reconstitution of the lyophilized formulation in the diluent, a final non-linear surfactant concentration of 1.41% (v/v) to about 2.24% (v/v).

12. The kit of claim 11, wherein the non-linear surfactant is present in the lyophilized far-red dye probe formulation at a concentration configured to produce, upon reconstitution of the lyophilized formulation in the diluent, a final non-linear surfactant concentration of 1.62% (v/v).

* * * * *

SEQUENCE LISTING

```
Sequence total quantity: 20
SEQ ID NO: 1            moltype = DNA  length = 45
FEATURE                 Location/Qualifiers
source                  1..45
                        mol_type = other DNA
                        organism = synthetic construct
misc_feature            1..12
                        note = RNA
misc_feature            13..45
                        note = DNA
misc_feature            13..45
                        note = Capture tail
SEQUENCE: 1
tctgttagtt cctttaaaaa aaaaaaaaaa aaaaaaaaaa aaaaa                 45

SEQ ID NO: 2            moltype = DNA  length = 16
FEATURE                 Location/Qualifiers
misc_feature            1..16
                        note = Synthetic Oligonucleotide
```

-continued

```
source                  1..16
                        mol_type = other DNA
                        organism = synthetic construct
SEQUENCE: 2
cggatgggtg agtaac                                                         16

SEQ ID NO: 3            moltype = DNA  length = 45
FEATURE                 Location/Qualifiers
misc_feature            1..45
                        note = Synthetic Oligonucleotide
regulatory              1..27
                        regulatory_class = promoter
source                  1..45
                        mol_type = other DNA
                        organism = synthetic construct
SEQUENCE: 3
aatttaatac gactcactat agggagataa gcccttacct tacca                         45

SEQ ID NO: 4            moltype = DNA  length = 45
FEATURE                 Location/Qualifiers
misc_feature            1..45
                        note = Synthetic Oligonucleotide
regulatory              1..27
                        regulatory_class = promoter
source                  1..45
                        mol_type = other DNA
                        organism = synthetic construct
SEQUENCE: 4
aatttaatac gactcactat agggagataa gccgttacct tacca                         45

SEQ ID NO: 5            moltype = DNA  length = 26
FEATURE                 Location/Qualifiers
source                  1..26
                        mol_type = other DNA
                        organism = synthetic construct
misc_feature            1..26
                        note = RNA
misc_feature            1..26
                        note = Synthetic Oligonucleotide
SEQUENCE: 5
gtctgggata ccacttggaa acagac                                              26

SEQ ID NO: 6            moltype = DNA  length = 21
FEATURE                 Location/Qualifiers
misc_feature            1..21
                        note = Synthetic Oligonucleotide
source                  1..21
                        mol_type = other DNA
                        organism = synthetic construct
misc_feature            1..21
                        note = RNA
SEQUENCE: 6
cactcacgca tgtctagagt g                                                   21

SEQ ID NO: 7            moltype = DNA  length = 50
FEATURE                 Location/Qualifiers
misc_feature            1..50
                        note = Synthetic Oligonucleotide
misc_feature            18..50
                        note = Capture tail
source                  1..50
                        mol_type = other DNA
                        organism = synthetic construct
misc_feature            1..17
                        note = RNA
misc_feature            18..50
                        note = DNA
SEQUENCE: 7
catgctccgc cgcttgtttt aaaaaaaaaa aaaaaaaaaa aaaaaaaaaa                    50

SEQ ID NO: 8            moltype = DNA  length = 25
FEATURE                 Location/Qualifiers
misc_feature            1..25
                        note = Synthetic Oligonucleotide
source                  1..25
                        mol_type = other DNA
                        organism = synthetic construct
SEQUENCE: 8
cttacctggg cttgacatgt gcctg                                               25
```

```
SEQ ID NO: 9            moltype = DNA  length = 45
FEATURE                 Location/Qualifiers
misc_feature            1..45
                        note = Synthetic Oligonucleotide
regulatory              1..27
                        regulatory_class = promoter
source                  1..45
                        mol_type = other DNA
                        organism = synthetic construct
SEQUENCE: 9
aatttaatac gactcactat agggagacac cacctgtgaa cctgc                    45

SEQ ID NO: 10           moltype = DNA  length = 24
FEATURE                 Location/Qualifiers
misc_feature            1..24
                        note = Synthetic Oligonucleotide
source                  1..24
                        mol_type = other DNA
                        organism = synthetic construct
misc_feature            1..24
                        note = RNA
SEQUENCE: 10
cctgcagaga tgtggtttcg cagg                                           24

SEQ ID NO: 11           moltype = DNA  length = 54
FEATURE                 Location/Qualifiers
misc_feature            1..54
                        note = Synthetic Oligonucleotide
misc_feature            22..54
                        note = Capture tail
source                  1..54
                        mol_type = other DNA
                        organism = synthetic construct
misc_feature            1..21
                        note = RNA
misc_feature            22..54
                        note = DNA
SEQUENCE: 11
gtaccgtcga tgtcttccct gtttaaaaaa aaaaaaaaaa aaaaaaaaaa aaaa          54

SEQ ID NO: 12           moltype = DNA  length = 16
FEATURE                 Location/Qualifiers
misc_feature            1..16
                        note = Synthetic Oligonucleotide
source                  1..16
                        mol_type = other DNA
                        organism = synthetic construct
SEQUENCE: 12
agcgttatcc ggattc                                                    16

SEQ ID NO: 13           moltype = DNA  length = 51
FEATURE                 Location/Qualifiers
misc_feature            1..51
                        note = Synthetic Oligonucleotide
regulatory              1..27
                        regulatory_class = promoter
source                  1..51
                        mol_type = other DNA
                        organism = synthetic construct
SEQUENCE: 13
aatttaatac gactcactat agggagattc ggaacccggc tcgagcttaa g             51

SEQ ID NO: 14           moltype = DNA  length = 24
FEATURE                 Location/Qualifiers
misc_feature            1..24
                        note = Synthetic Oligonucleotide
source                  1..24
                        mol_type = other DNA
                        organism = synthetic construct
misc_feature            1..24
                        note = RNA
SEQUENCE: 14
ccgctcaggc ggttgctcaa gcgg                                           24

SEQ ID NO: 15           moltype = DNA  length = 24
FEATURE                 Location/Qualifiers
misc_feature            1..24
                        note = Synthetic Oligonucleotide
```

-continued

```
source                  1..24
                        mol_type = other DNA
                        organism = synthetic construct
misc_feature            1..24
                        note = RNA
SEQUENCE: 15
ccgctcaggc ggttgctcaa gcgg                                          24

SEQ ID NO: 16           moltype = DNA  length = 57
FEATURE                 Location/Qualifiers
misc_feature            1..57
                        note = Synthetic Oligonucleotide
misc_feature            25..57
                        note = Capture tail
source                  1..57
                        mol_type = other DNA
                        organism = synthetic construct
misc_feature            1..24
                        note = RNA
misc_feature            25..57
                        note = DNA
SEQUENCE: 16
cgttcactat tggtctctgc attctttaaa aaaaaaaaaa aaaaaaaaaa aaaaaaa      57

SEQ ID NO: 17           moltype = DNA  length = 19
FEATURE                 Location/Qualifiers
misc_feature            1..19
                        note = Synthetic Oligonucleotide
source                  1..19
                        mol_type = other DNA
                        organism = synthetic construct
SEQUENCE: 17
gattatatag gacgacaag                                                19

SEQ ID NO: 18           moltype = DNA  length = 49
FEATURE                 Location/Qualifiers
misc_feature            1..49
                        note = Synthetic Oligonucleotide
regulatory              1..27
                        regulatory_class = promoter
source                  1..49
                        mol_type = other DNA
                        organism = synthetic construct
SEQUENCE: 18
aatttaatac gactcactat agggagagat gattgacttg tgattccgc               49

SEQ ID NO: 19           moltype = DNA  length = 23
FEATURE                 Location/Qualifiers
misc_feature            1..23
                        note = Synthetic Oligonucleotide
source                  1..23
                        mol_type = other DNA
                        organism = synthetic construct
misc_feature            1..23
                        note = RNA
SEQUENCE: 19
gcatggtgcg aattgggaca tgc                                           23

SEQ ID NO: 20           moltype = DNA  length = 14
FEATURE                 Location/Qualifiers
misc_feature            1..14
                        note = Synthetic Oligonucleotide
source                  1..14
                        mol_type = other DNA
                        organism = synthetic construct
SEQUENCE: 20
tttttttttt tttt                                                     14
```